United States Patent
Fulbright (10) Patent No.: US 11,912,285 B2
(45) Date of Patent: Feb. 27, 2024

(54) VEHICULAR PASSENGER MONITORING SYSTEM

(71) Applicant: University of South Carolina, Columbia, SC (US)

(72) Inventor: Ron Fulbright, Chesnee, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 151 days.

(21) Appl. No.: 17/569,776

(22) Filed: Jan. 6, 2022

(65) Prior Publication Data

US 2022/0212675 A1 Jul. 7, 2022

Related U.S. Application Data

(60) Provisional application No. 63/134,269, filed on Jan. 6, 2021.

(51) Int. Cl.
| | |
|---|---|
| *B60W 40/08* | (2012.01) |
| *G06V 20/59* | (2022.01) |
| *G06V 10/70* | (2022.01) |
| *G08B 17/10* | (2006.01) |
| *A61B 5/01* | (2006.01) |
| *A61B 5/08* | (2006.01) |
| *A61B 5/00* | (2006.01) |

(Continued)

(52) U.S. Cl.
CPC ............... *B60W 40/08* (2013.01); *A61B 5/01* (2013.01); *A61B 5/024* (2013.01); *A61B 5/0816* (2013.01); *A61B 5/6893* (2013.01); *B60W 60/00253* (2020.02); *G06V 10/70* (2022.01); *G06V 20/593* (2022.01); *G08B 17/10* (2013.01); *B60W 2540/043* (2020.02); *B60W 2540/221* (2020.02); *B60W 2556/45* (2020.02)

(58) Field of Classification Search
CPC .......... B60W 40/08; B60W 60/00253; B60W 2540/043; B60W 2540/221; B60W 2556/45; B60W 2420/42; A61B 5/01; A61B 5/024; A61B 5/0816; A61B 5/6893; A61B 5/0024; G06V 10/70; G06V 20/593; G06V 40/15; G08B 17/10; G08B 19/00

See application file for complete search history.

(56) References Cited

U.S. PATENT DOCUMENTS

| | | | |
|---|---|---|---|
| 10,275,670 B1 * | 4/2019 | Li | G06V 40/16 |
| 10,688,867 B2 * | 6/2020 | Wilson | G08B 25/016 |

(Continued)

*Primary Examiner* — Ryan W Sherwin
(74) *Attorney, Agent, or Firm* — BURR & FORMAN LLP (57) ABSTRACT

An apparatus for an autonomous vehicle may include a plurality of sensors and processing circuitry. The processing circuitry may be configured to receive a trip plan via including a pick-up location, a drop-off location, an identity of the passenger, and control parameters, execute the trip plan according to the pick-up location, the drop-off location, the identity of the passenger, and the control parameters, receive sensor data from the plurality of sensors, and analyze the sensor data in relation to a criteria profile to determine whether compliance boundaries of the criteria profile have been violated. The criteria profile may be generated based on the trip plan and may indicate compliance boundaries for the trip plan. The processing circuitry may be further configured to send an alert in response to determining that the sensor data indicates that a violation of a compliance boundary of the criteria profile has occurred.

17 Claims, 3 Drawing Sheets

(51) Int. Cl.
    *B60W 60/00*     (2020.01)
    *A61B 5/024*     (2006.01)

(56) References Cited

U.S. PATENT DOCUMENTS

| | | | |
|---|---|---|---|
| 11,106,927 B2* | 8/2021 | Reiley | G08B 3/10 |
| 11,393,238 B1* | 7/2022 | Kentley-Klay | B60W 40/08 |
| 11,613,268 B2* | 3/2023 | Liffman | G05D 1/0223 |
| | | | 701/24 |
| 2014/0309789 A1* | 10/2014 | Ricci | G06F 16/25 |
| | | | 700/276 |
| 2015/0314755 A1* | 11/2015 | Phelan | B60R 25/23 |
| | | | 701/2 |
| 2017/0330044 A1* | 11/2017 | Telpaz | G05D 1/0088 |
| 2018/0004211 A1* | 1/2018 | Grimm | G06Q 50/28 |
| 2020/0104617 A1* | 4/2020 | Herbst | G06V 40/20 |
| 2020/0164891 A1* | 5/2020 | Bender | B60W 50/0098 |
| 2020/0349666 A1* | 11/2020 | Hodge | G08G 1/017 |

* cited by examiner

VEHICULAR PASSENGER MONITORING SYSTEM

CROSS-REFERENCE TO RELATED APPLICATIONS

This application claims priority to U.S. Provisional Application No. 63/134,269, filed on Jan. 6, 2021, the contents of which are incorporated herein by reference in their entirety.

TECHNICAL FIELD

Example embodiments generally relate to self-driving or autonomous driving technologies and, more particularly, relate to apparatuses, systems, and methods for autonomous vehicle monitoring and providing feedback on vehicular passenger status and activity.

BACKGROUND

Many automobile manufacturers are currently involved in developing self-driving cars. Billions of dollars are being spent every year and the technology is progressing rapidly. Current rideshare options have adults as drivers that provide some degree of supervision over the activities of passengers, since some duty of care exists between the driver and the passenger. Also, rideshare vehicles are often owned by the driver and therefore the driver may have concern for the protection of the vehicle.

However, in the case of autonomous vehicles, the element of human supervision is lost. The dynamic decision making of a human, adult driver is no longer an involved in the passenger experience. As such, there is a risk that passengers may behave differently in the absence of a human driver. Also, the absence of a human driver eliminates any amount of societal levels of concern for others' health and well-being that an adult human driver may employ when delivering a passenger. It is therefore desirable to consider these changes that vehicular autonomy may bring and develop technical solutions to address the negative impacts of such changes.

BRIEF SUMMARY OF SOME EXAMPLES

New and unconventional systems, apparatuses, and methods are provided herein that are directed to, amongst other things, a combination of self-driving or autonomous vehicle technology and cognitive systems technology to produce, for example, an integrated virtual chaperone. In this regard, such an implementations, according to some example embodiments, may be embodied as or include an autonomous vehicle able to transport passengers to and from locations while also monitoring various aspects of the event (or trip) including the health and behavior of the passengers.

According to some example embodiments, a system is provided that comprises a supervisory device and a vehicle. The vehicle may be an autonomous vehicle. The supervisory device may be configured to receive, via a user interface, a trip plan. The trip plan may comprise a pick-up location and a drop-off location for a passenger for the trip plan, an identity of the passenger, and control parameters for the trip plan. The vehicle may comprise processing circuitry and a sensor network. The sensor network may comprise a plurality of sensors configured to capture sensor data relating to the vehicle and activities within the vehicle. The plurality of sensors may comprise a camera and a location sensor. The camera may have a field of view of an interior cabin of the vehicle. The processing circuitry may be in communication with a data communication network. A criteria profile may be generated by the supervisory device, the processing circuitry of the vehicle, or a network cloud entity, based on the trip plan. The criteria profile may indicate compliance boundaries for the trip plan. The processing circuitry may be configured to implement a chief stew module that configures the processing circuitry to receive the trip plan via the data communications network, execute the trip plan according to the pick-up location, the drop-off location, the identity of the passenger, and the control parameters, and receive sensor data from the sensor network. The processing circuitry may also be configured to analyze the sensor data in relation to the criteria profile to determine whether compliance boundaries of the criteria profile have been violated, and send an alert to the supervisory device or a third party device in response to determining that the sensor data indicates that a violation of a compliance boundary of the criteria profile has occurred.

According to some example embodiments, an example method for monitoring activity associated with a trip executed by an autonomous vehicle is provided. The method may comprise receiving a trip plan from a supervisory device via a data communications network, and executing, via processing circuitry of the autonomous vehicle, the trip plan according to a pick-up location, a drop-off location, an identity of a passenger, and control parameters specified for the trip plan. The example method may also comprise receiving sensor data from a sensor network. The sensor network may comprise a plurality of sensors disposed on the autonomous vehicle. The example method may also comprise analyzing the sensor data in relation to a criteria profile to determine whether compliance boundaries of the criteria profile have been violated. In this regard, the criteria profile may be based on the trip plan and may indicate compliance boundaries for the trip plan. The example method may also include sending an alert to the supervisory device or a third party device in response to determining that the sensor data indicates that a violation of a compliance boundary of the criteria profile has occurred.

According to some example embodiments, an apparatus is provided that comprises a plurality of sensors configured to capture sensor data relating to the vehicle and activities within the vehicle and processing circuitry in communication with a data communication network. The plurality of sensors may comprise a camera and a location sensor. The camera may have a field of view of an interior cabin of the vehicle. The processing circuitry may be configured to receive the trip plan via the data communications network. The trip plan may comprise a pick-up location, a drop-off location, an identity of the passenger, and control parameters. The processing circuitry may also be configured to execute the trip plan according to the pick-up location, the drop-off location, the identity of the passenger, and the control parameters. The processing circuitry may also be configured to receive sensor data from the plurality of sensors, and analyze the sensor data in relation to a criteria profile to determine whether compliance boundaries of the criteria profile have been violated. The criteria profile may be generated based on the trip plan and may indicate compliance boundaries for the trip plan. The processing circuitry may also be configured to send an alert in response to determining that the sensor data indicates that a violation of a compliance boundary of the criteria profile has occurred.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability, or configuration of the present disclosure. Rather, these example embodiments are provided so that this disclosure will satisfy applicable legal requirements. Like reference numerals refer to like elements throughout.

As used herein the term "or" is used as the logical or where any one or more of the operands being true results in the statement being true. As used herein, the phrase "based on" as used in, for example, "A is based on B" indicates that B is a factor that determines A, but B is not necessarily the only factor that determines A.

According to some example embodiments, an implementation, referred to in some instances as a vehicular virtual chaperone, is provided that employs a technical solution to the absence of oversight in an autonomous vehicle that may have be provided by a human adult driver in a conventional non-autonomous vehicle. According to some example embodiments, a vehicle system is provided that monitors and reports on activities related to and occurring within the vehicle using, for example, various cognitive systems. In this regard, some example embodiments may include an autonomous vehicle, which may be referred to as a date car, configured to chaperone, for example, teenagers as they embark on an outing such as, for example, a traditional "date," which may involve one or more people and a destination (e.g. movie, restaurant, event, etc.). However, example embodiments may also be employed in any context where some level of oversight may be helpful, such as, transporting children to school, sporting events, or the like. Additionally, some example embodiments may be employed when transporting the elderly to events including, for example, doctor's appointments. As such, according to some example embodiments, an implementation may be configured to transport anyone, children, adult, or the elderly, to and from any appointment including but not limited to: doctor/dentist appointment, lesson, practice, recital, play date, school. A self-driving car manufacturer or service employing automobiles may be some examples of entities that may implement various example embodiments of an autonomous vehicle as provided herein.

Example embodiments may provide a driverless service while ensuring safety of passengers, which may enable features to support operations that may be beneficial in various contexts including activities for teenagers. Some example embodiments may be added to or built on existing self-driving car technologies and platforms. Some example embodiments implemented in the context of a self-driving vehicle platform may provide driverless service while ensuring safety of passengers.

According to some example embodiments, an autonomous vehicle may be summoned by paying customers most probably via an app on a smart phone or a computer. The autonomous vehicle may begin the trip by autonomously navigating to a first pick-up location where one or more passengers enter the vehicle. The autonomous vehicle may then navigate to other pick-up locations and acquire additional passengers, if necessary. Once all passengers are onboard, the autonomous vehicle may then transport the passengers to one or more designated destinations. Passengers may optionally disembark at the destinations and reenter the autonomous vehicle at prescribed times and/or locations. The autonomous vehicle may then, for example, navigate back to designated drop-off locations (presumably the original pick-up locations, but not necessarily) and discharge the passengers bringing the trip to an end.

According to some example embodiments, before the trip begins, authorized customers (hereafter called supervisors) may specify a trip plan designating pick-up and drop-off locations, destinations, times, identities of passengers, and specifying any behavioral limitations. Such authorized customers or supervisors may provide this information to a system via an app on a smartphone, tablet, or computer but is not limited to this mode of communication. Once the trip is underway, supervisors may track the location of the autonomous vehicle at any time, in a number of different ways, via GPS or cell-phone tower triangulation for location, via on-board cameras for in cabin activity, and via various other sensors to provide a variety of information about the trip to the supervisors.

In this regard, at any time, for example, the system may be configured to permit supervisors to view live video of the inside of the autonomous vehicle and/or the area surrounding the autonomous vehicle. This may be done via cameras located within and outside the autonomous vehicle with data transmitted to a supervisory device wirelessly via, for example, the Internet. The supervisory device may also engage in video dialogue with the passengers at any time via microphones and speakers disposed within the cabin of the autonomous vehicle.

Additionally, according to some example embodiments, the supervisory device may be alerted to any noncompliance with a criteria profile that may be developed based on a trip plan. In this regard, the trip plan may indicate pic-up and drop-off locations, passenger identity, and control parameters. The control parameters may be configurable by a supervisor to tailor the criteria profile in accordance with various attributes such as, the age of the passengers, the event type (date, group outing, individual event, prom, concert, doctors appointment, etc.), the type of activities that may be permitted within the autonomous vehicle during the trip (e.g., drinking, smoking, music, etc. Such various parameters may be input by the supervisor to develop a criteria profile for the trip plan, which may define compliance boundaries for various behaviors and events. If the compliance boundaries are violated, an alert may be forwarded to the supervisory device to notify the supervisor. In this regard, according to some example embodiments, passengers may not be able to change routes or destinations, but events beyond control (e.g. accidents, road conditions, traffic conditions) may necessitate a change in the trip plan by the system. In such event, the supervisory device may be notified. Further, the supervisory device may be able to take control of the trip in real time to adjust parameters or end the trip. For example, via the supervisory device, a trip may be terminated at any time causing the autonomous vehicle to immediately navigate back to the designated drop-off locations to discharge the passengers. A supervisory device may be configured to permit changes to destinations and/or time parameters of the trip while the trip is in progress. Through the bidirectional video chat feature, passengers may be able to request changes in the trip plan from the supervisors. However, supervisors, via their devices, may be required to approve the changes before the autonomous vehicle will execute them.

In case of unforeseen emergencies, passengers may, according to some example embodiments, initiate an emergency stop from within the autonomous vehicle through interaction with the autonomous vehicle systems. When this happens, the autonomous vehicle may, for example, be configured to navigate to a safe location and allow the passengers to disembark. In this event, according to some example embodiments, the autonomous vehicle may automatically alert 911 (or any other first responders necessary) and alert the supervisory devices as to the occurrence and the change in the trip plan. In the case of mechanical malfunction of the autonomous vehicle itself, the system may task a new autonomous vehicle to pick up the passengers and either continue the trip or return passengers to designated drop-off locations.

According to some example embodiments, sensors (video, audio, and other types) within the autonomous vehicle may be configured to continuously monitor the behavior of the passengers by capturing data and supplying the data to processing circuitry for analysis. The detection of any prohibited behavior such as drinking alcoholic beverages, smoking, touching, kissing, vandalism, disruptive behavior, etc. may result in the immediate alerting of the supervisory device and possibly of first responders and/or the police. Passenger behavior may be analyzed by the processing circuitry and judged by a system within the autonomous vehicle trained to observe passengers and detect abnormal behavior, for example, via the application of sensor data to a criteria profile. Such functionality may be implemented in the context of a behavior module. The criteria profile that may be defined for identifying non-compliant behavior may be generated based on self-supervised deep machine learning giving the behavior module the ability to machine learn with experience and even machine learn from the behavior modules working in other autonomous vehicles.

According to some example embodiments, an autonomous vehicle may also be configured to continuously monitor aspects including the health of the passengers through video and other biosensors (e.g. video, audio, heart rate, respiration, etc.) disposed within the vehicle. Such functionalities may be implemented in the context of a health module. According to some example embodiments, the health module may also be a cognitive system and could also benefit from self-supervised deep learning, much like the behavior module. According to some example embodiments, the health module may be configured to detect, for example, an illness, stress, duress, or the like on the part of the passengers while in the autonomous vehicle. In the event any abnormal condition is detected, via comparison of health-related data to a criteria profile, (e.g., temperature via a temperature sensor in the form of a thermal camera, coughing or choking via audio or video, or the like), the autonomous vehicle may take immediate action such as alerting a supervisory device and/or first responders as necessitated by the type of condition.

According to some example embodiments, the autonomous vehicle may also comprise an entertainment module configured to engage the passengers with a variety of audio, video, and any Internet-based information authorized as part of the trip plan and associated criteria profile. For example, the entertainment module may have an on-board user interface or the entertainment module may be configured to wirelessly connect to the passengers' handheld electronic devices and permit the passenger devices to select and play music and/or video, or other entertainment content, through the in-car audio-visual system. According to some example embodiments, the entertainment module may enhance the enjoyment of the trip while in the autonomous vehicle, in a controlled manner.

According to some example embodiments, all operations of the autonomous vehicle may be monitored and controlled by an executive-level "watchdog" system, which may be referred to as the chief stew module. The chief stew module may, for example, be configured to support natural language interaction with the passengers and parents during the trip. The chief stew module may be configured to provide directions to the passengers, receive, and analyze questions, transmit answers, and also provide interesting facts and other information during the trip. The chief stew module may be an in-car entity that passengers and parents may interact with. However, the chief stew module may also be configured to monitor the behavior and actions associated with other modules, including a health module, the behavior module, and the entertainment module, as well as the self-driving operations of the car itself. The chief stew module may be configured to ensure the trip plan is progressing as intended and all subsystems are functioning well. As such, the chief stew module may be configured to command emergency actions and other deviations to the trip plan. In such a role, the chief stew module may be the entity through which supervisory devices communicate with to receive updates and notifications.

Figure 1:
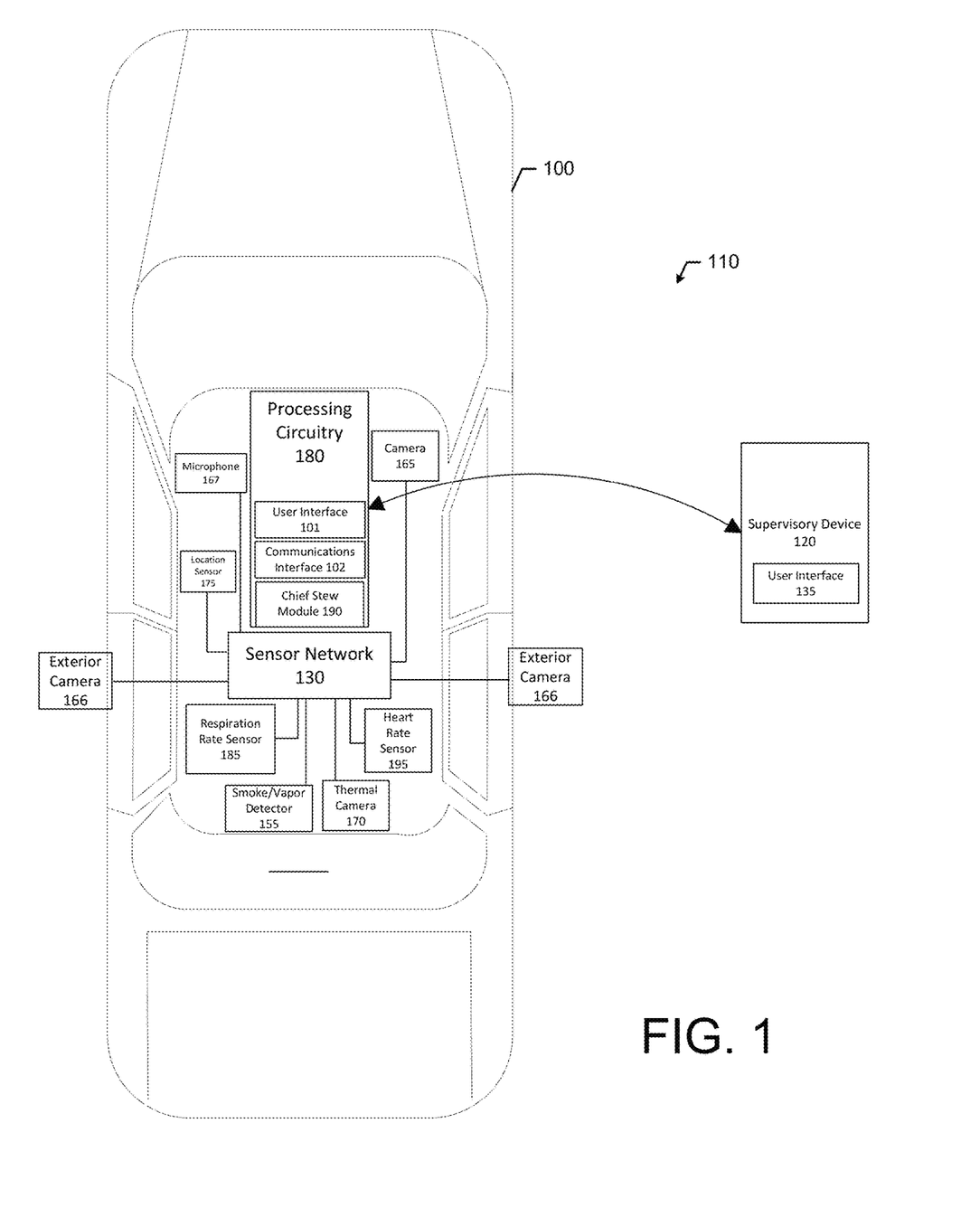
FIG. 1 illustrates an autonomous vehicle and various elements of a vehicular passenger monitoring system according to an example embodiment.

FIG. 1 illustrates a vehicle 100 comprising processing circuitry and a sensor network according to an example embodiment, as one example of a system. As can be seen in FIG. 1, the vehicle 100 may be included in a system 110. The system 110 may include a supervisory device 120 and the vehicle 100. The vehicle may comprise, amongst other components, a sensor network 130.

Although not shown, the vehicle 100 may be embodied as an autonomous automobile. As such, the vehicle 100 may comprise a motor and gearing for rotating wheels to move the vehicle 100. Further, the vehicle 100 may also include the necessary components and sensors to operate as an autonomous vehicle. In this regard, the vehicle 100 may include externally directed cameras and sensors to detect the road and the environment to perform autonomous operation. The vehicle 100 may be gas or battery powered. The vehicle 100 may also comprise a passenger cabin with safety features including seat belts, air bags, and the like.

The supervisory device 120 may be configured to receive, via a user interface 135, a trip plan. A supervisor, e.g., a parent, may be in possession of the supervisory device 120 and may enter the trip plan into the supervisory device 120. In this regard, via this entry, the supervisory device 120 may designate a pick-up and a drop-off location for a passenger for the trip plan, designate an identity of the passenger for the trip plan, and specify control parameters for the trip plan. As such, according to some example embodiments, the trip plan may comprise a pick-up and a drop-off location for the passenger, an identity of the passenger, and control parameters.

The vehicle 100 may comprise a sensor network 130 and processing circuitry 180. The sensor network 130 may comprise a plurality of sensors. In this regard, the plurality of sensors may be configured to capture sensor data relating to the vehicle and activities within the vehicle. The plurality of sensors may comprise a camera 165 and a location sensor 175. The camera 165 may have a field of view of an interior cabin of the vehicle. The sensor network 130 may also include a smoke/vapor detector 155, a respiration rate sensor 185, a heart rate sensor 195, and a thermal camera 170. The processing circuitry 180 may be in communication with a data communications network.

The processing circuitry 180 may be configured to implement a chief stew module 190. The chief stew module 190 may configure the processing circuitry 180 to perform various functionalities. In this regard, the processing circuitry 180 may be configured to receive the trip plan from the supervisory device 120 via the data communications network. In this regard, the processing circuitry 180 may receive the trip plan, or a variation of the trip plan, as a communication via a communications interface of the processing circuitry 180. The processing circuitry 180 may also be configured to execute the received trip plan according to the pick-up location, the drop-off location, the identity of the passenger, and the control parameters specified for the trip plan, monitor the passenger according to the trip plan. In this regard, the processing circuitry 180 may control the vehicle 100 to travel from the pick-up location to the drop-off location, for example, in accordance with a route that has been determined based on the pick-up location and the drop-off location (and possibly defined intermediate locations).

The processing circuitry 180 may also be configured to receive sensor data from the sensors of the sensor network 130. In this regard, different types of data may be captured and provided by different sensors. For example, the heart rate sensor 195 may capture heart rate data for provision to the processing circuitry 180 for analysis in comparison to a criteria profile. The sensor data may therefore be provided to the processing circuitry 180 via the individual sensors. In this regard, the wording "sensor network" is intended to mean a collection of sensors, without defining any manner in which the sensors are connected.

The processing circuitry 180 may therefore analyze the sensor data in relation to a criteria profile to determine whether compliance boundaries of the criteria profile have been violated. In this regard, the supervisory device 120, the processing circuitry 180, or a network entity connected to the supervisory device 120 and the processing circuitry 180, may be configured to generate a criteria profile. The criteria profile may be based on the various parameters that may be included in the trip plan. Based on the input parameters provided by a supervisor to the supervisory device 120, a trip plan data set may be generated that can be used to define various compliance boundaries. The compliance boundaries may be defined with respect to the sensor data that is being captured to determine if the sensor data falls outside of the compliance boundaries. For example, the criteria profile may be defined in the form of a heart rate range to be applied to heart rate data that may be provided by a heart rate sensor. In this regard, if the heart rate data indicates that a heart rate of a passenger is outside of a compliance boundary in the form of the heart rate range (i.e., too high or too low), then an action may be taken. While this is an example of one type of the compliance boundary that may be included in the criteria profile, it is understood that any number of compliance boundaries may be defined based on the same sensor data and combinations of sensor data (e.g., with weighting for certain data relative to other data).

Additionally, the processing circuitry 180 may be configured to send an alert to the supervisory device 120 or a third-party device in response to the sensor data being out of compliance with the criteria profile. The third-party device may be a supervisory device or receiver of a first responder or service provider. Being out of compliance may mean that the associated compliance boundary had been exceeded as defined by the content of the sensor data. In other words, the processing circuitry 180 may be configured to send an alert to the supervisory device or a third party device in response to determining that the sensor data indicates that a violation of a compliance boundary of the criteria profile has occurred.

The processing circuitry 180 of vehicle 100 may also include a user interface 101 and a communications interface 102. Further, the user interface 101 may be connected to, for example, a processor of the processing circuitry 180, such that the trip plan may be entered via the user interface 101 and received by the processing circuitry 180. Such an approach may involve a local entry of the trip plan for receipt. However, the processing circuitry 180 may also be connected to a network via the communications interface 102 and the trip plan may be received via this remote network connection, for example, to the supervisory device 120.

The vehicle 100 may be configured to supervise the passenger according to a criteria profile according to an example embodiment, as one example of a vehicle. The vehicle 100 may comprise processing circuitry 180 and a sensor network 130. The processing circuitry 180 may be connected to a network. The network may be a local network within the vehicle 100 or a wireless network. The sensor network 130 may comprise a plurality of sensors. The plurality of sensors may be configured to capture sensor data relating to the vehicle and activities such as drinking or smoking within the vehicle.

In an example embodiment, the plurality of sensors may include a heart rate sensor 195. The heart rate sensor 195 may be configured to capture a heart rate of the passenger of the vehicle 100. In this regard, the control parameters may include a predefined normal heart rate range for the heart rate sensor or the supervisor may be able to select a heart rate range when entering the trip plan. The heart rate range may be, for example, anywhere from 60 to 100 beats per minute. The processing circuitry 180 may be configured to analyze the sensor data, in this case the heart rate data, relative to the criteria profile. According to some example embodiments, the heart rate sensor 195 may be implemented in a number of ways. For example, the heart rate be detected by metal sensing pads that may be placed on the armrests in the cabin of the vehicle. Alternatively, an accelerometer capable of measuring small movements embedded in the seat belt to detect heart rate and generate heart rate data. Regardless of how the heart rate data is acquired, the data may be compared to the criteria profile and more particularly a heart-rate related compliance boundary of the criteria profile. The comparison may be made to determine if the heart rate data indicates that the passenger's heart rate is outside of the heart rate range. Further, in response to the heart rate of the passenger being outside of the heart rate range, an alert may be sent to the supervisory device 120 or to a third-party device.

According to some example embodiments, the plurality of sensors may include a respiration rate sensor 185. The respiration rate sensor 185 may be configured to capture a respiration rate of the passenger of the vehicle 100. The respiration rate sensor 185 may be implemented in a number of ways. For example, the image data captured by the camera 165 may be analyzed for movements indicative of breathing. As such, the camera 165 may be implemented as the respiration rate sensor 185. According to some example embodiments, the movements in the applied seat belt may be detected as indications of respiration and captured as respiration data. The seat belt may therefore be used as a component of the respiration rate sensor.

In this regard, the control parameters may include a predefined normal respiration rate range or a user-defined respiration rate range. The respiration rate range may be anywhere from, for example, 12 to 16 breaths per minute. The processing circuitry 180 may be configured to analyze the respiration data relative to the criteria profile. This may include comparing the respiration rate of the passenger to the respiration rate range of the respiration rate sensor 185. Further, in response to the respiration rate of the passenger being outside of the predefined normal respiration rate range, an alert may be sent to the supervisory device 120 or to a third-party device.

Further, a combination of data captured by, for example, the heart rate sensor and data captured by the respiration rate sensor may be analyzed and compared by the processing circuitry 180. The combination of data may further be compared to the criteria profile provided for the trip plan. Accordingly, an alert may be sent to the supervisory device 120 or a third-party device indicating the combination of data being outside of a combination range provided in the criteria profile.

In an example embodiment, the plurality of sensors may include a thermal camera 170. The thermal camera 170 may be configured to capture a temperature in the form of heat data. In this regard, the control parameters may include a predefined normal body temperature range or a user-defined body temperature range for the thermal camera 170. The body temperature range for the thermal camera may be anywhere from 97° F. (36.1° C.) to 99° F. (37.2° C.). The processing circuitry 180 may be configured to analyze the heat data relative to the criteria profile. This may include comparing the body temperature of the passenger to the body temperature range of the thermal camera. Further, in response to the body temperature of the passenger being outside of the predefined normal body temperature range, an alert may be sent to the supervisory device 120 or to a third-party device.

According to some example embodiments, other heat-related criteria may be defined via the control parameters of the trip plan. In this regard, heat-related criteria may include no smoking and no vaping. The thermal camera 170 may be configured to capture thermal images that the processing circuitry 180 may use to detect heat signatures that are indicative of the smoking or vaping. For example, if a high heat location is imaged near a passenger's mouth (and possibly repeatedly imaged near the passenger's mouth, then the image may be indicative of a smoking or vaping event. The detection of the smoking or vaping event may be compared to the criteria profile, and more specifically a compliance boundary for smoking or vaping, to determine if a non-compliance has occurred and an alert should be sent.

The camera 165 and/or the thermal camera 170 may further detect various other behaviors of an individual or multiple passengers through image analysis. In this regard, acts of aggression, displays of affection, drinking, passing or sharing of items, and other physical behaviors may be determined based on image analysis and compared to the criteria profile. In this regard, any behavior such as drinking alcoholic beverages, smoking, physical behavior between the passengers, vandalism, disruptive behavior, or suspected behaviors may be detected and compared to the criteria profile to determine appropriate action to take. Accordingly, an alert may be sent to the supervisory device 120 or a third-party device, in response to the behavior being out of compliance with the criteria profile. The processing circuitry 180 may send an alert to the supervisory device 120 or a third-party device in response to data being out of compliance.

In an example embodiment, the plurality of sensors may include a smoke and/or vape detector 155. The smoke and/or vape detector 155 may be configured to detect cigarette, THC, and vape smoke in the cabin of the vehicle 100. Further, the smoke and/or vapor detector 155 may detect specific compounds contained in the smoke, such as the detection of THC emitted from marijuana smoking. In this regard, the control parameters may include a predefined normal sensitivity range for fire detection, signaling, and emergency communications, as defined by NFPA 72 (National Fire Alarm and Signaling Code), published by the National Fire Protection Association or user-defined parameters and ranges may be set as a smoke-related parameter of the control parameters. The processing circuitry 180 may be configured to analyze the smoke data provided by the smoke/vapor sensor 155 relative to the criteria profile. This may include comparing the contents of the smoke or vapor detected in the cabin of the vehicle 100 to compliance boundaries set by the criteria profile. Further, in response to a detection of smoke being outside of the criteria profile, an alert may be sent to the supervisory device 120 or to a third-party device.

According to some example embodiments, the plurality of sensors may further comprise one or more exterior cameras 166. The exterior cameras 166 may have selected fields of view or a panoramic view of an exterior surrounding of the vehicle 100. According to some example embodiments, the external cameras 166 may be components of and/or used for a navigation system of the autonomous vehicle. According to some example embodiments, the exterior cameras 166 may be configured to capture images of or detect a passenger or an object surrounding the exterior of the vehicle 100. Further, the exterior cameras 166 may capture images of or detect the passenger entering and exiting the cabin of the vehicle 100.

According to some example embodiments, the control parameters may be defined that are associated with the image or detection data provided by the exterior cameras 166. For example, control parameters may be set that are used to generate related compliance boundaries of the criteria profile, for example, for the passenger to only be able to exit the vehicle 100 at a drop-off location of the trip plan or in the case of an emergency stop. If the passenger exits, for example, at another location, the processing circuitry 180 may send an alert due to the non-compliance. Additionally, the control parameters may defined to include obtain an identity of the passenger or object surrounding the exterior of the vehicle. The processing circuitry 180 may be configured to analyze the identity provided by the exterior camera 166 relative to the criteria profile. This may include comparing the identity of the passenger or object surrounding the exterior of the vehicle 100 to compliance boundaries set by the criteria profile with respect to identity. Further, in response to a detection of the identity of the passenger or object being outside of the criteria profile, an alert may be sent to the supervisory device 120 or to a third-party device.

The chief stew module 190 may also configure the processing circuitry 180 to receive the trip plan from the supervisory device 120, via the data communications network, execute the trip plan according to the pick-up location, the drop-off location, the identity of the passenger, and the control parameters specified for the trip plan, monitor the passenger according to the trip plan, analyze the sensor data in relation to a criteria profile based on the trip plan, and send an alert to the supervisory device 120 or a third party device in response to the sensor data being out of compliance with the criteria profile. In this regard, a determined route may be an element of the criteria profile, and the occurrence of a route deviation (e.g., due to a car accident or other need for detour) may be a non-compliance with the criteria profile, and may cause an alert to be sent.

Example embodiments described herein may be applied as a retrofit to an autonomous vehicle (e.g., that does not include some or all of sensor network 130), or example embodiments may be integrated into the systems of the autonomous vehicle that may be used for other purpose. In this regard, the processing circuitry 180 may include or embody processing circuitry that may be used by an autonomous vehicle for other purposes (i.e., for navigation and the like). As such, some example embodiments may be integrated into newly manufactured autonomous vehicles. The processing circuitry 180 may therefore be configured to operate and control navigation functions of the vehicle 100, as well as operate and control various other autonomous vehicle systems of the vehicle 100. In contrast, the processing circuitry 180 may be separate from the existing processing circuitry of the autonomous vehicle and may be in communication with such autonomous vehicle systems via a local or remote network. Furthermore, the processing circuitry 180 may communicate with existing sensors within the autonomous vehicle. In this regard, processing circuitry 180 of the apparatus may be in communication with the vehicle systems of the autonomous vehicle via the data communications network. Accordingly, processing circuitry 180 may be used for other purposes in the autonomous vehicle, but may also be configured to implement a chief stew module that configures the processing circuitry 180 to receive the trip plan via the data communications network, execute the trip plan according to the pick-up location, the drop-off location, the identity of the passenger, and the control parameters, receive sensor data from the sensor network, analyze the sensor data in relation to the criteria profile to determine whether compliance boundaries of the criteria profile have been violated; and send an alert to the supervisory device or a third party device in response to determining that the sensor data indicates that a violation of a compliance boundary of the criteria profile has occurred.

The sensor network 130 may further comprise a microphone 167. The microphone 167 may be configured to support natural language interaction with the passenger and the supervisory device 120 during the trip plan. The microphone 167 may be housed inside the cabin of the vehicle 100 or may be housed on the exterior of the vehicle 100. Further, the microphone 167 may detect noise levels below 10 dB-A as well as above 23 dB-A. Accordingly, the microphone 167 may capture sound data for application to the criteria profile to determine if a related non-compliance has occurred. In this regard, the control parameters may be selected with respect certain noises that may be indicative of a behavior that is not desired or permitted. For example, the control parameters may be defined with respect to screaming, yelling, any high decibel sounds (e.g., relative to a threshold), speech (e.g., inappropriate or violent language), other suspicious noises, or the like. The control parameters may be defined with respect to sounds within the cabin of the vehicle 100 or external to the vehicle 100. The processing circuitry 180 may be configured to analyze the sound data provided by the microphone 167 relative to the criteria profile. This may include comparing sound date to one more compliance boundaries set by the criteria profile based on the control parameters. Further, in response to sound data indicating a violation of the criteria profile, an alert may be sent to the supervisory device 120 or to a third-party device.

Figure 2:
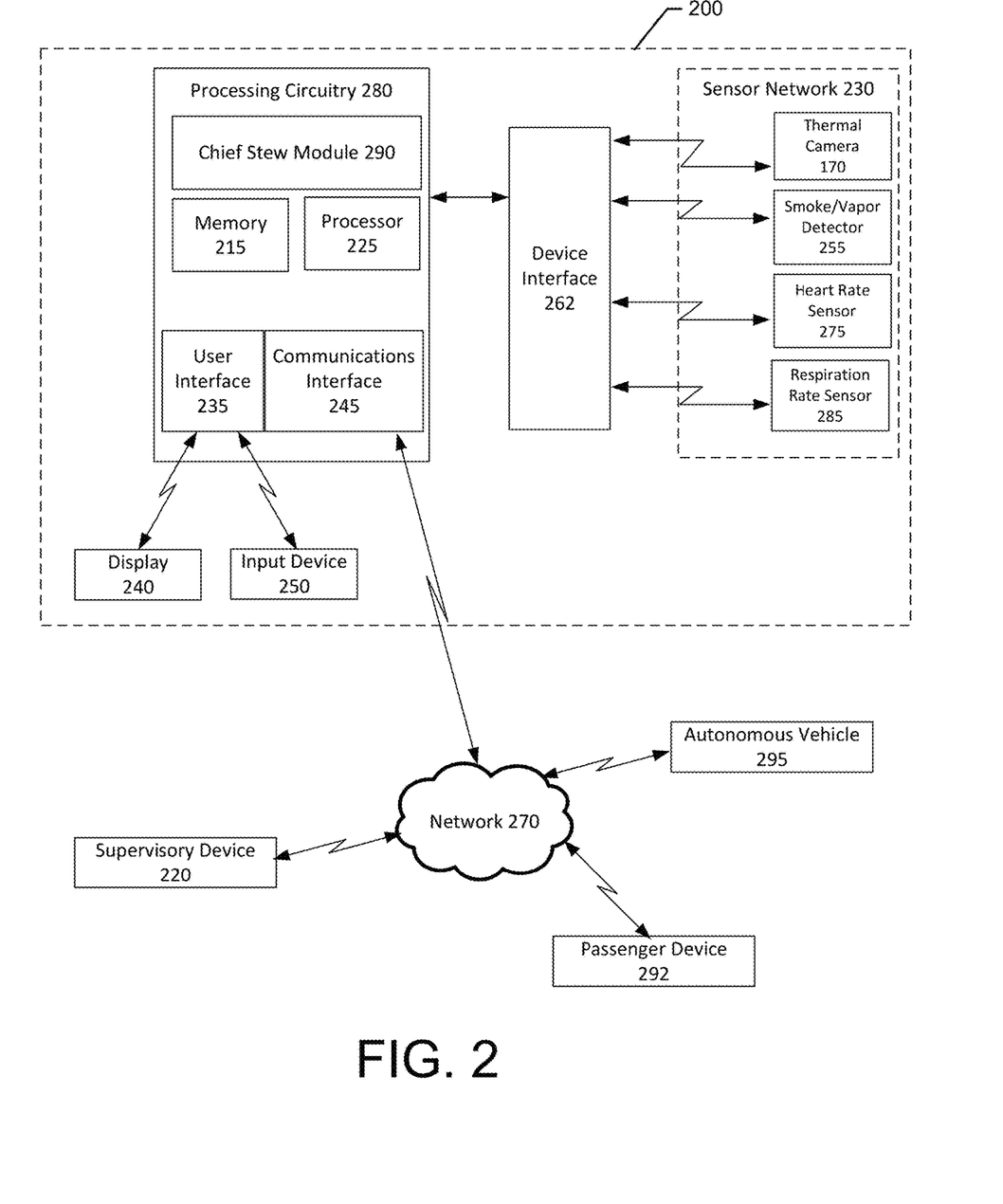
FIG. 2 illustrates a block diagram of components of an apparatus element of a monitoring system according to an example embodiment.

FIG. 2 is a block diagram of some components of an autonomous vehicle 200 that may be in communication with a supervisory device 220, a passenger device 292, and another autonomous vehicle 295. With respect to FIG. 2, an example configuration of the autonomous vehicle 200 is provided as a more detailed block diagram. In this regard, autonomous vehicle 200 may comprise processing circuitry 280. Processing circuitry 280 may, in turn, comprise a processor 225, a memory 215, the chief stew module 205, a user interface 235, and a communications interface 245. Additionally, the autonomous vehicle 200 may include additional components not shown in FIG. 2 and the processing circuitry 280 may be operably coupled to other components of the autonomous vehicle 200 that are not shown in FIG. 2. The processing circuitry 280 may be configured in the same or similar manner as the processing circuitry 180, as described herein, to control the operation of the vehicle 200. The vehicle 200 may be the same or similar to the vehicle 100.

The vehicle 200 may comprise a sensor network 230 and processing circuitry 280. The sensor network 230 may comprise a plurality of sensors and may be same or similar to the sensor network 130. In this regard, the plurality of sensors may be configured to capture sensor data relating to the vehicle and activities within the vehicle. The plurality of sensors may comprise a camera 265 and a location sensor 275. The camera 265 may have a field of view of an interior cabin of the vehicle. The processing circuitry 280 may be in communication with a data communications network. The processing circuitry 280 may be configured to implement a chief stew module 290. The chief stew module 290 may configure the processing circuitry 280 to further receive the trip plan from the supervisory device 220 via the data communications network, execute the trip plan according to the pick-up location, the drop-off location, the identity of the passenger, and the control parameters specified for the trip plan, monitor the passenger according to the trip plan, analyze the sensor data in relation to a criteria profile based on the trip plan, and send an alert to the supervisory device 120 or a third-party device in response to the sensor data being out of compliance with the criteria profile. As such, the chief stew module 290 may configured the processing circuitry 280 to operate in the same or similar manner as the chief stew module 190 configures the processing circuitry 180.

Further, the user interface 235 may be connected to a network and the network may be a local network within the autonomous vehicle 200 or a wireless network. Accordingly, the trip plan may be received via a local network connection to the supervisory device 220. Conversely, the trip plan may be received via a remote network connection to the supervisory device 220.

The autonomous vehicle 200 may be configured to supervise the passenger according to a criteria profile according to an example embodiment, as one example of a vehicle 200. The vehicle 200 may comprise processing circuitry 280 and a sensor network 230. The processing circuitry 280 may be connected to a network. The network may be a local network within the vehicle 200 or a wireless network. The sensor network 230 may comprise a plurality of sensors. The plurality of sensors may be configured to capture sensor data relating to the vehicle and activities such as drinking or smoking within the vehicle.

According to some example embodiments, the vehicle 200 and, more specifically, the processing circuitry 280, the chief stew module 290, and the sensor network 130 may operate in the same or in a similar manner as the like-named components of vehicle 100. As such, the components of the vehicle 200 may be configured to function similarly. As such, the vehicle 200 may be configured to implement aspects of example embodiments in the context of an individual apparatus.

According to some example embodiments, processing circuitry 280 may be in operative communication with or embody, the memory 215, the processor 225, the user interface 235, and the communications interface 245. Through configuration and operation of the memory 215, the processor 225, the user interface 235, and the communications interface 245, the processing circuitry 280 may be configurable to perform various operations as described herein, including the operations and functionalities described with respect to the chief stew module 290. In this regard, the processing circuitry 280 may be configured to perform computational processing, memory management, user interface control and monitoring, and manage remote communications, according to an example embodiment. In some embodiments, the processing circuitry 280 may be embodied as a chip or chip set. In other words, the processing circuitry 280 may comprise one or more physical packages (e.g., chips) including materials, components or wires on a structural assembly (e.g., a baseboard). The processing circuitry 280 may be configured to receive inputs (e.g., via peripheral components), perform actions based on the inputs, and generate outputs (e.g., for provision to peripheral components). In an example embodiment, the processing circuitry 280 may include one or more instances of a processor 225, associated circuitry, and memory 215. As such, the processing circuitry 280 may be embodied as a circuit chip (e.g., an integrated circuit chip, such as a field programmable gate array (FPGA)) configured (e.g., with hardware, software or a combination of hardware and software) to perform operations described herein.

In an example embodiment, the memory 215 may include one or more non-transitory memory devices such as, for example, volatile or non-volatile memory that may be either fixed or removable. The memory 215 may be configured to store information, data, applications, instructions or the like for enabling, for example, the functionalities described with respect to the processing circuitry 280 and the chief stew module 290. The memory 215 may operate to buffer instructions and data during operation of the processing circuitry 280 to support higher-level functionalities, and may also be configured to store instructions for execution by the processing circuitry 280. The memory 215 may also store various information including trip information and plans, criteria profiles, sensor data, etc. According to some example embodiments, various data stored in the memory 215 may be generated based on other data and stored or the data may be retrieved via the communications interface 245 and stored in the memory 215.

As mentioned above, the processing circuitry 280 may be embodied in a number of different ways. For example, the processing circuitry 280 may be embodied as various processing means such as one or more processors 225 that may be in the form of a microprocessor or other processing element, a coprocessor, a controller or various other computing or processing devices including integrated circuits such as, for example, an ASIC (application specific integrated circuit), an FPGA, or the like. In an example embodiment, the processing circuitry 280 may be configured to execute instructions stored in the memory 215 or otherwise accessible to the processing circuitry 280. As such, whether configured by hardware or by a combination of hardware and software, the processing circuitry 280 may represent an entity (e.g., physically embodied in circuitry—in the form of processing circuitry 280) capable of performing operations according to example embodiments while configured accordingly. Thus, for example, when the processing circuitry 280 is embodied as an ASIC, FPGA, or the like, the processing circuitry 280 may be specifically configured hardware for conducting the operations described herein. Alternatively, as another example, when the processing circuitry 280 is embodied as an executor of software instructions, the instructions may specifically configure the processing circuitry 280 to perform the operations described herein.

The communications interface 245 may include one or more interface mechanisms for enabling communication with other devices external to the autonomous vehicle 200, via, for example, network 270, which may, for example, be a local area network, the Internet, or the like, through a direct (wired or wireless) communication link to another external device, or the like. In some cases, the communications interface 245 may be any means such as a device or circuitry embodied in either hardware, or a combination of hardware and software that is configured to receive or transmit data from/to devices in communication with the processing circuitry 280. The communications interface 245 may be a wired or wireless interface and may support various communications protocols (WIFI, Bluetooth, cellular, or the like). Via the network 270, the vehicle 200 may be configured to communicate with the supervisory device 220, the passenger device 290, or another autonomous vehicle 295.

The user interface 235 may be controlled by the processing circuitry 280 to interact with peripheral components or devices of the vehicle 200 that can receive inputs from a user or provide outputs to a user. In this regard, via the user interface 235, the processing circuitry 280 may be configured to receive inputs from an input device 250 which may be, for example, a touch screen display, a keyboard, a mouse, a microphone, or the like. The user interface 235 may also be configured to provide control and outputs to peripheral devices such as, for example, a display 240 (e.g., a touch screen display), speaker, or the like. The user interface 235 may also produce outputs, for example, as visual outputs on a display, audio outputs via a speaker, or the like.

The vehicle 200 may also include a device interface 262, which may be a component of the processing circuitry 280. The device interface 262 may be configured to connect the processing circuitry 280 to various peripheral device such as sensors. In this regard, the device interface 262 may be configured to connect the processing circuitry 280 to the thermal camera 270, the smoke/vapor detector 255, the heart rate sensor 275, and the respiration rate sensor 285, each of which may be leveraged to implement the various functionalities described The chief stew module 290 may, according to some example embodiments, be circuitry that is part of or a configuration of the processor 225, possibly in combination with the memory 215. As such, the chief stew module 290 may be configured to cause the processing circuitry 280 to perform various functionalities as a component of the processing circuitry 280. As such, the chief stew module 290, and thus the processing circuitry 280, may be configured to implement the functionality of various example embodiments of an autonomous vehicle described herein, which may include the functionalities of the chief stew module 290, the health module, the entertainment module, and the behavior module.

Figure 3:
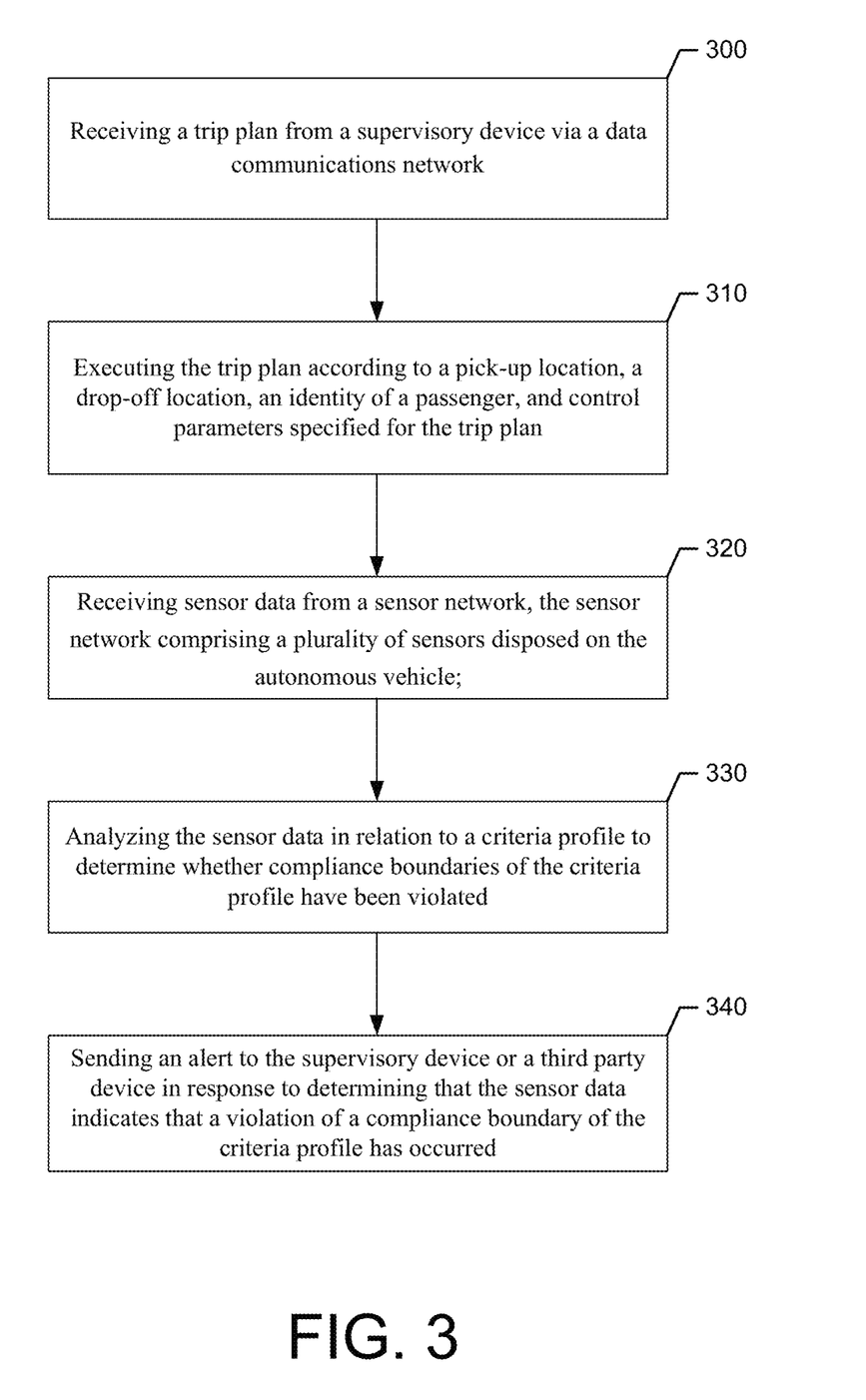
FIG. 3 illustrates a block diagram of a method of monitoring and supervising a passenger according to a trip plan, according to an example embodiment.

FIG. 3 illustrates a flowchart diagram of the method of supervising a passenger according to a criteria profile in accordance with an example embodiment. The method is described in steps 300-340 of FIG. 3. The method of FIG. 3 may be implemented to by the processing circuitry 180 or the processing circuitry 280, as described herein.

The system of some embodiments may include additional features, modifications, augmentations and/or the like to achieve further objectives or enhance performance of the system. The additional features, modifications, augmentations and/or the like may be added in any combination with each other. As provided herein various additional features, modifications, and augmentations that can each be added individually or in any combination with each other. For example, the criteria profile may be an autonomous vehicle profile. In an example embodiment, the trip plan may be received via a local network connection to the supervisory device. In some cases, the trip plan may be received via a remote network connection to the supervisory device. In an example embodiment, the chief stew module may be configured to house a health module. In some cases, the chief stew module may house an entertainment module. In some cases, the chief stew module may house a behavior module.

As used herein, the term "module" is intended to include a computer-related entity, such as but not limited to hardware, software, or a combination of hardware and software. For example, a module may be, but is not limited to being a software or hardware implementation of a process, an object, an executable, and/or a thread of execution, which may be implemented via a processor or computer. By way of example, both an application running on a computing device and/or the computing device can be a module. One or more modules can reside within a process and/or thread of execution and a module may be localized on one computer and/or distributed between two or more computers. In addition, these modules can execute from various computer readable media having various data structures stored thereon. The modules may communicate by way of local and/or remote processes such as in accordance with a signal having one or more data packets, such as data from one module interacting with another module in a local system, distributed system, and/or across a network such as the Internet with other systems by way of the signal. Each respective module may perform one or more functions that will be described in greater detail herein. However, it should be appreciated that although such examples are described in terms of separate modules corresponding to various functions performed, some examples need not necessarily utilize modular architectures for employment of the respective different functions. Thus, for example, code may be shared between different modules, or the processing circuitry itself may be configured to perform all of the functions described as being associated with the modules described herein. Furthermore, in the context of this disclosure, the term "module" should not be understood as a nonce word to identify any generic means for performing functionalities of the respective modules. Instead, the term "module" should be understood to be a modular entity that is specifically configured in, or can be operably coupled to, processing circuitry to modify the behavior and/or capability of the processing circuitry based on the hardware and/or software that is added to or otherwise operably coupled to the processing circuitry to configure the processing circuitry accordingly.

Various aspects of the above example embodiments of the autonomous vehicle and the associated system may be developed based on scenarios and other factors to control the self-driving vehicle. The following provides example embodiment approaches and considerations that may be used for designing and implementing aspects of the example embodiments described herein.

In this regard, Christensen's jobs theory may be used as a way to identify future scenarios for traditional scenario planning and demonstrate with a case study involving the future of self-driving automobiles. Traditionally, to determine what a future product or service should be like, customers are asked to express what features or characteristics they desire. However, jobs theory queries future customers keying on the motivation behind using the product or service thereby exposing different kinds of innovation opportunities. Using jobs theory as a front-end to scenario planning identifies unique future scenarios to be explored in the scenario planning phase.

Scenario planning may be a method to make flexible long-term strategic plans based on imagining several possible futures. Once used only in the military intelligence arena, many companies and organizations now use scenario planning across a number of industries. The process of scenario planning may begin with a discussion about how trends and shifts in society, economics, politics, and technology might affect a particular issue going into the future. From this, a list of priorities may be identified and used to form sketches of the future. Since scenario planning has been used in a variety of industries, over the decades many diverse definitions of scenarios have arisen. Definitions of scenarios include: Description of a complex future situation reflecting different perspectives; forecasts of future business environments; description of a possible set of events that might reasonably take place; and scenarios tell a story of how various elements might interact under certain conditions.

A common thread through these definitions may be the idea of "describing possible futures." Scenario planning may be used for innovation. By describing future scenarios, innovations can be realized that are needed to evolve the current state of the art into the imagined future. Scenario planning may include how one goes about identifying the future scenarios. Scenario planning may involve extending observed trends into the future. While this is certainly a useful approach, considering the future differently might lead to identifying different kinds of futures. Querying users and customers called "jobs-to-be done" theory (hereafter called "jobs theory") may be used.

According to jobs theory, people bring products and services into their lives to make progress toward a goal. Rephrasing the question of user needs in this way is helpful because it relies on the motivation behind using something rather than functional characteristics. This takes focus away from a specific existing product or service and exposes user needs not fulfilled by any existing product or service.

A method is therefore proposed using jobs theory as a "front-end" to traditional scenario planning. Expressing the needs of customers in the future as jobs to be done may open up the space of innovative ideas by considering scenarios traditional scenario planning techniques would miss. Such an approach may be used for self-driving automobiles.

Innovation may be characterized in many ways over the decades and innovations vary widely in scope and effect. Technological innovation as "creative destruction" whereby the existing may be replaced by the new thus driving entire economies forward. Innovation may be responsive to opportunities in a market. Opportunities may be present due to continually changing market conditions, knowledge, processes, user needs, demographics, culture, and customer behavior.

Sustaining innovation can be determined as being incremental, evolutionary improvements and disruptive innovation as discontinuous, radical, revolutionary leaps forward. Disruptive innovations are often breakthrough innovations or platform innovations resulting in changes to an entire market and user behavior. Major innovative successes like these usually drive the creation of a family of complimentary products and services.

These kinds of descriptions rely on the scope or effect of an innovation. Another way to describe innovation is based on motivation. Sibling innovations may be described as new products and services arising because of, and in service of, other innovations such as breakthrough and platform innovations. Derivative innovation may be identified to refer to adaptation of innovative concepts to another domain. Me-too innovation refers to a company's first entrance into a market to compete with others already in the market. Induced innovation describes invention forced by the reduction of costs among competitors. Frugal innovation involves the reduction of complexity and features to appeal to low-end customers in a market. Eco-friendly innovations and sustainability innovations are driven by environmental impact concerns. Innovation does not always come in the form of new products. Rather, innovation can occur anywhere in the business process. Innovation designed to improve or revolutionize the user experience is called experience innovation, UX innovation, or service innovation. Innovation applied anywhere in the system of organizations, people, activities, and resources involved in moving resources supplier to consumer is supply chain innovation. Innovation in the manufacturing, production, or delivery of goods and services is process innovation. Innovation relating in general to the way a company or organization operators is business model innovation.

There are also many different views of innovation management and governance. The black box model of innovation can be traced back to viewing innovation as opaque process into which one supplies funding and innovations somehow emerge. The linear model of innovation envisions innovation to be a step-by-step process. Innovations are seen as proceeding through research and development, production, and sales/marketing phases.

The technology push model (also called the manufacturer push model) involves an innovative idea originating within a company or organization and being pushed through development into the market without end-user involvement. Innovative ideas originating with end users is called demand pull innovation, market pull innovation, or user pull innovation because the idea is pulled from the demand side into the development cycle.

Many feel the phase-gate structure suggested by linear models does not match reality. Instead, innovation is a complex interplay of ideas and communication among many people in different roles. A chain-linked model acknowledges the research, development, production, and marketing phases of linear models but includes feedback loops and iterative cycles among the phases.

The agile model of innovation was developed extending concepts from agile software development methodologies to the management of innovation. Agile methods seek to reduce risk and limit resource expenditures by employing the "design-a-little" build-a-little" principle. The open innovation model acknowledges the distribution of knowledge and expertise across companies, organizations, and industries. For example, companies should seek out and use intellectual property from others and also seek to actively export any internal innovations or proprietary knowledge to others to inspire innovation elsewhere. This openly collaborative approach to innovation is embodied in the connect & develop innovation model, itself a combination of open and user pull methods. The milieu model of innovation acknowledges the importance of a mutually supportive network of social relationships, knowledge, and expertise in a limited geographical area with Silicon Valley being the canonical example.

The crowdsourcing model of innovation has seen success via Internet sites. Collaborative innovation networks (CoINs) describe diverse teams of collaborators working together on innovations using social media and the Internet as the medium of discourse. The directed evolution model differs from traditional innovation models because it guides evolution of a technological system toward a chosen future. The future is chosen based on a set of general evolutionary patterns gleaned from the study of technological systems over several decades.

The goal of any innovation methodology is to ensure an enterprise creates products and services future customers are going to need and want to buy. A first step in that process is to know what customers are going to want and need in the future. Scenario planning is similar to directed evolution in both rely on projecting trends into the future.

Jobs theory is a kind of demand/user pull approach but is based on the motivation behind using the product or service. Here, we are not talking about the altruistic or ethical types of motivation behind ecofriendly, sustainability, frugal innovations. Instead, jobs theory keys on personal motivations like being healthy, being safe, being smarter, etc. Both scenario planning and jobs theory seek to identify Drucker-like market opportunities to which an enterprise can respond. If these market opportunities are far enough of the current state of the art and current market, one can produce a disruptive, breakthrough, or platform innovation.

With respect to scenario planning, scenarios are descriptions of the future. The approach one uses to foresee the future determines the kind of scenario developed and the vocabulary used. Accordingly, in some instances, eighteen different kinds of scenarios have been identified (1) Decision Scenarios—to inform decision-making; (2) Orientation Scenarios—intelligence about the future; (3) Systems Scenarios—has control over; (4) External Scenarios—does not have control over; (5) External Projects—generated externally; (6) Internal Projects—generated internally; (7) Process Scenarios—certain path forward; (8) Situational Scenarios—uncertain path forward; (9) Anticipative Scenarios—start in future/work backward; (10) Explorative Scenarios—start in present/work forward; (11) Normative Scenarios—probable or preferred futures; (12) Descriptive Scenarios—describing the natural future; (13) Prediction Scenarios—futures with probabilities; (14) Projection Scenarios—futures without probabilities; (15) Extreme Scenarios—consider extreme dynamics; (16) Trend Scenarios—forecasting general trends; (17) Short-Range Scenarios—two years or less into future; (18) Long-Range Scenarios—five years or more into future; and (19) Explorative scenarios, prediction scenarios, projection scenarios, trend scenarios, and long-range scenarios start with the present and project into the future. For example, in innovation, current customers are usually asked what features or characteristics a future version of a product or service should have. This kind of projection usually results in short term or sustaining innovations and ignores the fact the best future product or service may be something entirely different than the current product or service.

Jobs theory, however, is a different way to identify user needs. Jobs theory is based on the idea people invite products and services into their lives to perform a job. Customers seek progress—movement toward a goal or aspiration—and use products and services to make progress ("jobs"). By understanding customers' goals, one can better envision and develop desirable innovations.

Understanding the functional, social, and emotional aspects of a customer's decision to use a product or service is the key to understanding why a customer chooses a product or service. Asking the job a product or service performs for a customer is a fundamentally different way of user needs analysis. For example, to improve sales, a prominent fast-food chain asked its customers what kind of new milkshakes they wanted. Customers responded and the chain provided many new flavor options yet sales did not increase. It was observed that the chain was selling milkshakes in the early morning and also in the afternoon so asked customers why they bought milkshakes at those times of the day.

It was found that early morning customers were looking for a breakfast item they could enjoy while in a long commute to work. However, afternoon customers were buying treats for their children as a reward or as a way to gain quality time with the child. Customers were buying the same product but for different reasons. The chain increased sales by offering more and different breakfast items suitable for long commutes. Understanding the reason a customer invites a product of service into their lives is the key to jobs theory.

Realizing asking about customer's motivation yields a different view caused consideration of using jobs theory as a front-end to scenario planning. The idea is considering future motivations first will identify different types of scenarios to examine. This idea begs the question: would these new scenarios be significantly different than the scenarios we would normally come up with?

To explore this question, the future of the self-driving automobile was considered. Most people expect this technology to be a reality in the coming years, but consideration should be made of how this new technology going to change how we live, work, and play and what products/services will be needed in this new future? The basic characteristics of the future technology includes self-driving, voice-activated/natural language interfaces, constantly connected to the Internet, integrated fully with passenger's smartphones, tablets, and social media, on-demand multimedia entertainment, and integration with in-home virtual assistants.

To imagine the future based on traditional scenario planning, it was first asked what an automobile is used for today. The items represent a future scenario for the automobile. How does a self-driving automobile affect these scenarios? If a person does not have to drive, they can spend the time in the automobile involved in other pursuits. This changes the role the automobile plays in a customer's life. For example, instead of the automobile just transporting someone to work, the person could actually do some of the work while in transit.

Therefore, automobiles of the future can have equipment and services designed to facilitate in-car work, as the "virtual office" role. Instead of just sitting and riding to a vacation or trip, the smart, self-driving automobile of the future should be able to participate in preparing the family for the vacation or trip, as the "virtual travel agent" role. The automobile may therefore transport me to/from work, go on a vacation/trip, drive to a restaurant, go shopping, travel to meetings/appointments, let others borrow the car, get the car washed, and have the car repaired.

While riding to a restaurant in a self-driving car of the future, passengers should be able to peruse the restaurant's menu, ask questions about dishes, and even place orders while in transit, as the "virtual wait staff" role. Instead of just being transported to a store to do some shopping, the automobile of the future should be an active participant in the shopping experience much like a sales representative for the store. The person should be able to see specials, items on sale, and inquire about items of interest and even ask for advice, as the "virtual sales rep" role. While being transported to a meeting or appointment in a self-driving automobile, the car should help prepare for the meeting by briefing the person, displaying relevant information, facilitating communication with others, and even giving some advice for the upcoming meeting, as the "virtual administrative assistant" role.

Finally, instead of the owner having to drive to the repair shop or the carwash, a self-driving automobile should be able to drive itself. Furthermore, if the owner has given permission for someone else to use it, a self-driving automobile should be able to drive itself to the borrower's location, as the "virtual chauffer" role. Therefore, by first taking typical uses of an automobile in the present and imagining how self-driving technology will change these in the future, we have identified several new roles for the future self-driving automobiles. Those roles include "virtual office" facilitating in-car work; "virtual travel agent" services; "virtual wait staff" capability for any restaurant; "virtual sales rep" for any store; "virtual administrative assistant;" and "virtual chauffer."

Using scenario planning, each of the roles can be used to develop a detailed description of future scenarios in which the automobile performs each of the "virtual" roles listed. Doing so, will generate a lengthy list of specific requirements for the future automobile. These future requirements can be used to drive innovative efforts today in order to build the imagined future automobile. However, the roles identified for future self-driving automobiles using traditional scenario planning are not surprising or unexpected. What is the purpose of using a technique that generates results we already have? We next explored the idea of looking at the future differently using jobs theory.

Since the essence of jobs theory is to discover the customers' motivations, the basic motivations every person has may be identified. The motivations may include keep me safe, keep my child safe, keep me healthy, keep me happy, make me smarter, take me places, and run errands for me.

The items listed are the answers to the question asked of a future customer "Why did you use your self-driving automobile?" These define a completely different set of roles, or services the future self-driving automobile must provide. These roles or services include "virtual baby sitter," "virtual chaperone," "virtual bodyguard," "virtual doctor/ nurse," "virtual counselor," "virtual teacher/coach/mentor," "virtual chauffer," "virtual personal assistant."

Currently, it is unsafe, and even against the law in some areas, to leave a child in the car unattended while you shop in a store. What if the automobile was the safest place to leave your child? What if the automobile was the safest place for you to be? The self-driving automobile of the future could be a virtual baby sitter and virtual bodyguard able to take action to avoid harm to the occupant such as drive away from a threat, drive to a police station, drive to a hospital, or drive back home.

Every teenager wants to date before their parents are ready for them to be out on their own and before they can drive themselves. As a virtual chaperone, the self-driving automobile of the future should be able to drive your teenager and his or her date to and from a destination and ensure their safety. Time spent in an automobile is valuable contact time during which one's health could be monitored by the self-driving automobile of the future as a virtual doctor/nurse. What if the self-driving automobile became an active partner in our physical and mental health? With the automobile doing the driving, that time becomes a great time to have an in-depth one-on-one conversation with a virtual counselor.

Everyone wants to learn new things, have new things explained to them, or keep up with the latest news and developments. Because it will have our attention for several hours a week, the self-driving automobile of the future should be our virtual teacher, educator, and mentor. People today use their automobile to run errands.

What if the self-driving automobile of the future could run errands for us? Imagine, the automobile driving itself to the car wash or repair station. But, above, we imagined that with just traditional scenario planning. Imagine instead of "taking the keys away" from an elderly parent, having the self-driving car carry them everywhere they want to go (and also monitor their well-being along the way). A virtual chauffer gives us years of continued independence. Personal assistants help organize the lives of busy people with too many demands on their time and attention. What if the self-driving automobile (or a small fleet of self-driving automobiles) could serve as a virtual personal assistant and even run errands for us? By asking about our motivations, the jobs we want done, we have arrived at an entirely different set of roles for the automobile of the future.

Scenario planning is a powerful method for creating descriptions of possible futures and has been proven over time. However, how to decide which scenarios one chooses to describe is a crucial detail. Using Christensen's jobs theory is a way to identify scenarios different from those one might encounter using traditional scenario planning. The future of the self-driving automobile can be considered. Using traditional scenario planning, today's uses may be projected into the future. There is no doubt self-driving technology will change these uses and it is certainly a valuable exercise to develop future scenario descriptions for each use case. We then used jobs theory to identify possible future scenarios. In jobs theory one asks the future customer why they use a product or service thereby exposing the motivation behind the usage. When we ask this about the self-driving automobile we arrive at a set of quite different future scenarios. In these scenarios, the self-driving automobile becomes an active and collaborative partner in one's life (baby sitter, body guard, doctor, teacher, mentor, counselor, assistant, etc.)

Many modifications to the example embodiment provided herein, as well as other example embodiments, will come to mind to one skilled in the art to which these example embodiments pertain having the benefit of the teachings presented in the foregoing descriptions and the associated drawings. Therefore, it is to be understood that the example embodiments are not to be limited to the specific ones disclosed and that modifications and other embodiments are intended to be included within the scope. Moreover, although the foregoing descriptions and the associated drawings describe example embodiments in the context of certain example combinations of elements or functions, it should be appreciated that different combinations of elements or functions may be provided by alternative embodiments without departing from the scope. In this regard, for example, different combinations of elements or functions than those explicitly described above are also contemplated. In cases where advantages, benefits or solutions to problems are described herein, it should be appreciated that such advantages, benefits or solutions may be applicable to some example embodiments, but not necessarily all example embodiments. Thus, any advantages, benefits or solutions described herein should not be thought of as being critical, required, or essential to all embodiments or to that which is claimed herein. Although specific terms are employed herein, they are used in a generic and descriptive sense only and not for purposes of limitation.

That which is claimed:

1. A system comprising:
a supervisory device configured to receive, via a user interface, a trip plan, the trip plan comprising:
a pick-up location and a drop-off location for a passenger for the trip plan;
an identity of the passenger; and
control parameters for the trip plan, the control parameters comprising a heat-related criterion; and
a vehicle comprising processing circuitry and a sensor network, the vehicle being an autonomous vehicle;
wherein the sensor network comprises a plurality of sensors configured to capture sensor data relating to the vehicle and activities within the vehicle, the plurality of sensors comprising a camera and a location sensor, the camera comprising a thermal camera, wherein the camera has a field of view of an interior cabin of the vehicle and is configured to capture heat data of the passenger;
wherein the processing circuitry is in communication with a data communication network;
wherein a criteria profile is generated by the supervisory device, the processing circuitry of the vehicle, or a network cloud entity, based on the trip plan, the criteria profile indicating compliance boundaries for the trip plan;
wherein the processing circuitry is configured to implement a chief stew module that configures the processing circuitry to:
receive the trip plan via the data communications network;
execute the trip plan according to the pick-up location, the drop-off location, the identity of the passenger, and the control parameters;
receive sensor data from the sensor network;
analyze the sensor data in relation to the criteria profile to determine whether compliance boundaries of the criteria profile have been violated;
send an alert to the supervisory device or a third party device in response to determining that the sensor data indicates that a violation of a compliance boundary of the criteria profile has occurred;

analyze the heat data relative to the heat-related criterion as provided in the criteria profile;
send the alert in response to determining the heat data violated the heat-related criterion; and
wherein the heat data is indicative of a physical behavior of more than one passenger in the interior cabin of the vehicle.

2. The system of claim 1, wherein the control parameters comprise a heart rate range;
wherein the plurality of sensors further comprises a heart rate sensor, wherein the heart rate sensor is configured to capture heart rate data indicating a heart rate of the passenger;
wherein the chief stew module configures the processing circuitry to:
analyze the heart rate data relative to the heart rate range as provided in the criteria profile; and
send the alert in response to determining that the heart rate data is outside of the heart rate range.

3. The system of claim 1, wherein the control parameters comprise a respiration range;
wherein the plurality of sensors further comprises a respiration rate sensor, wherein the respiration rate sensor is configured to capture respiration data indicating a respiration rate of the passenger;
wherein the chief stew module configures the processing circuitry to:
analyze the respiration data relative to the respiratory range as provided in the criteria profile; and
send the alert in response to determining that the respiration data is outside of the respiratory range.

4. The system of claim 1, wherein the criteria profile comprises a multi-dimensional well-being compliance boundary based on a heart rate range and a respiration range;
wherein the plurality of sensors further comprises a heart rate sensor, wherein the heart rate sensor is configured to capture heart rate data indicating a heart rate of the passenger;
wherein the plurality of sensors further comprises a respiration rate sensor, wherein the respiration rate sensor is configured to capture respiration data indicating a respiration rate of the passenger;
wherein the processing circuitry is configured to:
aggregate the heart rate data and the respiration data into a multi-dimensional well-being data set;
analyze the multi-dimensional well-being data set in relation to the multi-dimensional well-being compliance boundary; and
send the alert to the supervisory device or third-party device in response to the multi-dimensional well-being data set violating the multi-dimensional well-being compliance boundary.

5. The system of claim 4, wherein the heart rate sensor is located in an armrest of the vehicle.

6. The system of claim 1, wherein the thermal camera detects physical behavior between the passengers.

7. The system of claim 1, wherein the heat-related criteria is determined based on images captured by the thermal camera and analyzed via machine learning to determine signatures for physical behaviors of passengers within the cabin.

8. The system of claim 1, wherein the control parameters comprise a smoke-related criterion;
wherein the plurality of sensors further comprises a smoke detector, wherein the smoke detector is configured to detect smoke within the interior cabin of the vehicle and provide smoke data;
wherein the chief stew module configures the processing circuitry to:
analyze the smoke data relative to the smoke-related criterion as provided in the criteria profile; and
send the alert in response to determining that the smoke data violates the smoke-related criterion.

9. The system of claim 1, wherein the chief stew module further configures the processing circuitry to:
determine a travel route based on the trip plan;
receive location data from the location sensor;
analyze the location data relative to the travel route as provided in the criteria profile; and
send the alert in response to determining that the location data violates the travel route.

10. A method for monitoring activity associated with a trip executed by an autonomous vehicle, the method comprising:
receiving a trip plan from a supervisory device via a data communications network;
executing, via processing circuitry of the autonomous vehicle, the trip plan according to a pick-up location, a drop-off location, an identity of a passenger, and control parameters specified in the trip plan, the control parameters comprising a heat-related criterion;
receiving sensor data from a sensor network, the sensor network comprising a plurality of sensors disposed on the autonomous vehicle, the plurality of sensors comprising a thermal camera having a field of view of an interior cabin of the vehicle and configured to capture heat data of the passenger;
analyzing the sensor data in relation to a criteria profile to determine whether compliance boundaries of the criteria profile have been violated, the criteria profile being based on the trip plan and indicating compliance boundaries for the trip plan;
sending an alert to the supervisory device or a third party device in response to determining that the sensor data indicates that a violation of a compliance boundary of the criteria profile has occurred;
analyzing the heat data relative to the heat-related criterion as provided in the criteria profile; and
sending the alert in response to determining that the heat data violates the heat-related criterion;
wherein the heat data is indicative of a physical behavior of more than one passenger in the cabin of the vehicle.

11. The method of claim 10, wherein the sensor network comprises a camera having a field of view of an interior cabin of the autonomous vehicle.

12. The method of claim 10, wherein the trip plan is received via a remote network connection to the supervisory device.

13. The method of claim 10 further comprising:
determining a travel route based on the trip plan;
receiving location data from a location sensor, the location sensor being one of the plurality of sensors of the sensor network;
analyzing the location data relative to the travel route as provided in the criteria profile; and
sending the alert in response to determining that the location data violates the travel route.

14. An apparatus implemented in association with an autonomous vehicle, the apparatus comprising:
a plurality of sensors configured to capture sensor data relating to the vehicle and activities within the vehicle, the plurality of sensors comprising a camera and a location sensor, the camera having a field of view of an interior cabin of the vehicle; and processing circuitry in communication with a data communication network;

wherein the processing circuitry is configured to:
receive a trip plan via the data communications network, the trip plan comprising a pick-up location, a drop-off location, an identity of the passenger, and control parameters, the control parameters comprising a heat-related criterion;

execute the trip plan according to the pick-up location, the drop-off location, the identity of the passenger, and the control parameters;

receive sensor data from the plurality of sensors, the plurality of sensors comprising a thermal camera having a field of view of an interior cabin of the vehicle and configured to capture heat data of the passenger;

analyze the sensor data in relation to a criteria profile to determine whether compliance boundaries of the criteria profile have been violated, wherein the criteria profile is generated based on the trip plan and indicates compliance boundaries for the trip plan;

send an alert in response to determining that the sensor data indicates that a violation of a compliance boundary of the criteria profile has occurred;

analyze the heat data relative to the heat-related criterion as provided in the criteria profile; and send the alert in response to determining that the heat data violated the heat-related criterion, wherein the heat data is indicative of a physical behavior of more than one passenger in the cabin of the vehicle.

15. The apparatus of claim 14, wherein the control parameters comprise a heart rate range;

wherein the plurality of sensors further comprises a heart rate sensor, wherein the heart rate sensor is configured to capture heart rate data indicating a heart rate of the passenger;

wherein the processing circuitry is configured to:
analyze the heart rate data relative to the heart rate range as provided in the criteria profile; and
send the alert in response to determining that the heart rate data is outside of the heart rate range.

16. The apparatus of claim 14, wherein the control parameters comprise a respiration range;

wherein the plurality of sensors further comprises a respiration rate sensor, wherein the respiration rate sensor is configured to capture respiration data indicating a respiration rate of the passenger;

wherein the processing circuitry is configured to:
analyze the respiration data relative to the respiratory range as provided in the criteria profile; and
send the alert in response to determining that the respiration data is outside of the respiratory range.

17. The apparatus of claim 14, wherein the control parameters comprise a smoke-related criterion;

wherein the plurality of sensors further comprises a smoke detector, wherein the smoke detector is configured to detect smoke within the interior cabin of the vehicle and provide smoke data;

wherein the processing circuitry is configured to:
analyze the smoke data relative to the smoke-related criterion as provided in the criteria profile; and
send the alert in response to determining that the smoke data violates the smoke-related criterion.

* * * * *

UNITED STATES PATENT AND TRADEMARK OFFICE
CERTIFICATE OF CORRECTION

| | | |
|---|---|---|
| PATENT NO. | : 11,912,285 B2 | Page 1 of 1 |
| APPLICATION NO. | : 17/569776 | |
| DATED | : February 27, 2024 | |
| INVENTOR(S) | : Ron Fulbright | |

It is certified that error appears in the above-identified patent and that said Letters Patent is hereby corrected as shown below:

In the Claims

In Column 23, Claim 1, Line 3, "the heat data violated" should read --that the heat data violates--.

In Column 25, Claim 14, Line 28, "violated" should read --violates--.

Signed and Sealed this
Thirtieth Day of April, 2024

Katherine Kelly Vidal
*Director of the United States Patent and Trademark Office*